United States Patent [19]

Shinmen et al.

[11] Patent Number: 5,211,953
[45] Date of Patent: May 18, 1993

[54] LIVER FUNCTION IMPROVER

[75] Inventors: Yoshifumi Shinmen, Nagaokakyo; Kengo Akimoto, Mishima; Sumio Asami, Ibaraki; Yoshihide Suwa, Ibaraki; Yoshinori Kitagawa, Ibaraki; Michihiro Sugano, Fukuoka; Hideaki Yamada; Sakayu Shimizu, both of Kyoto, all of Japan

[73] Assignee: Suntory, Limited, Osaka, Japan

[21] Appl. No.: 902,854

[22] Filed: Jun. 23, 1992

Related U.S. Application Data

[62] Division of Ser. No. 555,586, Jul. 20, 1990, Pat. No. 5,180,588.

[30] Foreign Application Priority Data

Jul. 21, 1989 [JP] Japan ............................ 1-187497
Apr. 3, 1990 [JP] Japan ............................ 2-087500

[51] Int. Cl.$^5$ ........................ A61K 47/00; A01N 43/30
[52] U.S. Cl. .................................... 424/439; 514/464; 514/811; 514/893; 514/894
[58] Field of Search ............... 424/439; 514/464, 811, 514/893, 894

[56] References Cited

U.S. PATENT DOCUMENTS

| | | | |
|---|---|---|---|
| 4,427,694 | 1/1984 | Benecke | 514/811 |
| 4,868,207 | 9/1989 | Shi-jie | 514/464 |
| 4,904,694 | 2/1990 | Matsuoka | 514/464 |
| 4,996,235 | 2/1991 | Robertson | 514/811 |
| 5,066,669 | 11/1991 | Iwasaki | 514/464 |

FOREIGN PATENT DOCUMENTS 1046380 10/1966 United Kingdom .

*Primary Examiner*—Thurman K. Page
*Assistant Examiner*—D. Gabrielle Phelan
*Attorney, Agent, or Firm*—Burns, Doane, Swecker & Mathis

[57] ABSTRACT

A liver function improver, food, or drink comprising, as an effective ingredient, a dioxabicyclo[3.3.0]octane derivative, such as sesamin, sesaminol espisesamin, episesaminol, sesamolin, 2-(3,4-methylenedioxyphenyl)-6-(3-methoxy-4-hydroxyphenyl)-3,7-dioxabicyclo[3.3.-0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

18 Claims, No Drawings

LIVER FUNCTION IMPROVER

This application is a divisional of application Ser. No. 07/555,586, filed Jul. 20, 1990, now U.S. Pat. No. 5,180,588.

BACKGROUND OF THE INVENTION

1. Field of the Invention

The present invention relates to a liver function improver comprising, as an effective ingredient, dioxabicyclo[3.3.0]octane derivative, and to a food or drink containing this derivative having a liver function-improving action, a cholesterol level-reducing action, and/or a neutral fat level-reducing action.

2. Description of the Related Art

The liver is the largest substantial organ of a human body, in addition to the brain, and has various functions such as a detoxifying action, carbohydrate metabolism, protein metabolism, the formation and secretion of bile, the formation of blood coagulation factors, hormone-controlling action, and the action of storing various living body constituents such as fat, glycogen, proteins, and vitamins. These functions are acutely or chronically impeded by viruses, drugs, poisons, excessive intake of alcohol, malnutrition, liver circulatory system troubles, bile duct occlusion and the like, and as a result, there appear such diseases as viral hepatitis, drug doxic hepatitis, alcoholic hepatitis, congestive hepatitis, liver disorder due to a stagnation of hepatic juice fatty liver, interus, and finally, hepatocirrhosis.

For example, to remedy liver disorder caused by alcohol, there has been adopted not only a method of controlling an intake of meat fat and an excessive intake of alcohol, but also a medicinal therapy using antihistamic agents, barbituric acid salts, adenosine triphosphate (ATP), pyrazole, a mixture of dihydroxy acetone and riboflavin, glucronic acid, arginine hydrochloride, and amino acid preparations such as glutathione. Nevertheless, the effects of these drugs are not satisfactory, and there is no certain remedial method other than a control of an excessive intake of alcohol. As one of the causes of liver disorder brought on by drugs and poisons, there can be mentioned the formation of a harmful oxygen free radical, and accordingly, a large quantity of glutathione is administered for theraphy of toxicoses and allergic diseases. Especially, for a protection of cells, glutathione reduces or extinguishes an active oxygen species or free radical by glutathione peroxidase, or glutathione reacts with a poison through glutathione-S-tranferase and discharges the poison from cells in the form of a glutathione conjugate, to exert the intended function whereby antioxidation, detoxification and a protection from radiation damage can be achieved. Nevertheless, even if glutamine per se is administered, the half-life is short (only several minutes) and tissue glutathione is not effectively increased. Accordingly, the development of glutathione derivatives and the like is now under investigation.

Under the above circumstances, however, the development of a novel liver function improver is urgently required.

SUMMARY OF THE INVENTION

Therefore, a primary object of the present invention is to provide a novel liver function improver and a food having a liver function-improving action.

Since the liver-derived enzyme activity [glutamic-oxaloacetic aminotransferase (GOT) and glutamic-pyruvic aminotransferase (GPT)] in sera of mouse and rat is increased by liver disorder, to obtain the above-mentioned object, the inventors searched for a liver function improver by using GOT and GPT as indications, and as a result, found that a dioxabicyclo[3.3.0]octane isolated from sesame seeds, sesame lees, and sesame oil, or a synthesized dioxabicyclo[3.3.0]octane derivative, has a liver function-improving action, a cholesterol level-reducing and a neutral fat level-reducing action, and is very safe.

More specifically, in accordance with the present invention, there is provided a liver function improver comprising, as an effective ingredient, a dioxabicyclo[3.3.0]octane derivative represented by the following general formula (1):

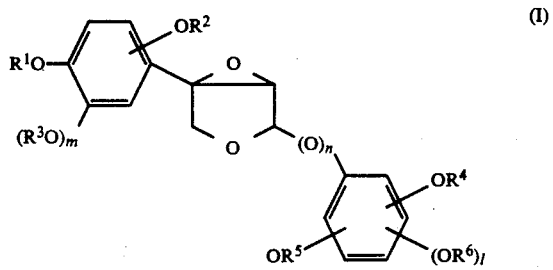

wherein $R^1$, $R^2$, $R^3$, $R^4$, $R^5$, and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

Furthermore, in accordance with the present invention, there is provided a food containing the above-mentioned derivative.

DESCRIPTION OF THE PREFERRED EMBODIMENTS

As the dioxabicyclo[3.3.0]octane, in the present invention, sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane can be used. These derivatives can be used alone or in the form of a mixture of two or more thereof.

The compound of the present invention, and an extract composed mainly of the compound of the present invention, can be obtained according to the following procedures. First, an extract composed mainly of the compound of the present invention can be obtained from sesame oil according to a method comprising extracting sesame oil with an organic solvent substantially immiscible with sesame oil and capable of extracting and dissolving the compound of the present invention, and concentrating the extract. As the organic solvent, there can be mentioned, for example, acetone, methylethylketone, diethylketone, methanol and ethanol. For example, an extract composed mainly of the compound of the present invention can be obtained by mixing sesame oil homogeneously with an organic solvent as mentioned above, allowing the mixture to stand at a low temperature, carrying out a phase separation according to a customary process, and removing the solvent from the solvent fraction by evaporation. More specifically, sesame oil is dissolved in 2 to 10 volumes, preferably 6 to 8 volumes of acetone, and the solution is allowed to stand at −80° C. overnight. As a result, the oil component is precipitated, and the organic solvent is removed from the obtained filtrate by distillation, whereby an extract composed mainly of the compound of the present invention is obtained. Alternatively, sesame oil is mixed with hot methanol or hot ethanol, the mixture is allowed to stand at room temperature, and the solvent is removed from the solvent fraction to obtain an extract composed mainly of the compound of the present invention. More specifically, sesame oil is mixed with hot methanol (higher than 50° C.) or hot ethanol (higher than 50°) in a volume 2 to 10 times, preferably 5 to 7 times, as large as the volume of the sesame oil to effect a violent extraction. The phase separation is effected by a phase separation when standing at room temperature or a centrifugal separation according to customary procedures, and the solvent is removed from the solvent fraction by distillation to obtain an extract composed mainly of the compound of the present invention. Furthermore, the supercritical gas extraction can be utilized. The compound of the present invention can be obtained from an extract as mentioned above by treating the extract by a customary method such as column chromatography, high performance liquid chromatography, recrystallization, distillation, or liquid-liquid countercurrent distribution chromatography. More specifically, by using a reversed phase column ($5C_{18}$) and methanol/water (60/40) as the eluent, the extract is subjected to high performance liquid chromatography, the solvent is removed by distillation, and the obtained crystal is recrystallized from ethanol to obtain the compound used in the present invention, such as sesamin, episesamin, sesaminol or episesaminol. The sesame oil used in the present invention can be either a purified product or a crude product. Furthermore, sesame seeds or sesame less (defatted sesame seeds having a residual oil content of 8 to 10%) can be used. In this case, sesame seeds or sesame less are pulverized if necessary, and then subjected to the extraction according to customary procedures using an any solvent, for example, a solvent as mentioned above with respect to the extraction from sesame oil. The extraction residue is separated, and the solvent is removed from the extract by evaporation or the like to obtain an extraction product. The compound used in the present invention, for example, sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane, can be obtained from a sesame seed extract, a sesame lee extract or a crude sesame oil extract according to the same procedures as described above. Moreover, the compound used in the present invention can be obtained from a by-product formed in the sesame oil-preparing process.

The process for the purification of the compound of the present invention and the process for obtaining the extract are not limited to those mentioned above, and the compound used in the present invention and the extract composed mainly of the compound of the present invention are not limited to those obtained from sesame oil, sesame lees and sesame seeds, but as is apparent to persons with ordinary skill in the art, all natural substances containing the compound used in the present invention can be used. For example, there can be mentioned *Acanthopanax sessiliflorus*, paulowina, Ginkgobiolobu and Piper lonum.

The following processes can be adopted for the synthesis of the compound of the present invention.

For example, sesamin and episesamin can be synthesized according to the process of Beroza et al. [J. Am. Chem. Soc., 78, 1242 (1956)]. Pinoresinol [in the general formula (I), $R^1$ and $R^4$ represent H, $R^2$ and $R^5$ represent $CH_3$, and n, m and l are zero] can be synthesized according to the process of Freundenberg et al. [Chem. Ber., 86, 1157 (1953)]. Furthermore, syringaresinol [in the general formula (I), $R^1$ and $R^4$ represent H, $R^2$, $R^3$, $R^3$, $R^5$ and $R^6$ represents $CH_3$, n is zero, and each of m and l is 1] can be synthesized according to the process of Freundenberg et al [Chem. Ber., 88, 16 (1955)].

The compound used in the present invention also can be used in the form of a glycoside. Furthermore, compounds used in the present invention can be used alone or in combination with other liver function improver or a functional factor of a food.

The liver function improver of the present invention can be orally administered, or non-orally administered, for example, by intramuscular injection, hypodermic injection or intravenous injection.

The dosage depends on the state of a person to whom the liver function improver is administered, but in general, in the case of the oral administration, the dosage is 1 to 100 mg/day, and in the case of the non-oral administration, the dosage is 0.1 to 20 mg/day. For the preparation of an injection, a solubilizing agent for a drug, for example, a nonionic surface active agent, can be used. More specifically, the compound of the present invention is dissolved under heating in a nonionic surface active agent such as POE (60) hardened castor oil or POE sorbitan-monooleate in a volume 80 times as large as the volume of the compound of the present invention, and the solution is diluted with a physiological saline to form an injection solution. An isotonic agent, a stabilizer, an antiseptic agent, and an alagesic agent, can be incorporated according to need. If necessary, the compound of the present invention can be formed into an emulsion, a capsule, a dust, a granule or a tablet.

In view of the cholesterol level-reducing action and the neutral fat level-reducing action, it is considered preferable to incorporate the compound of the present invention into foods containing oil and fat, although the kind of food into which the compound of the present invention is incorporated is not limited. For example, there can be mentioned natural foods such as meat, fish and nut, foods to which oil and fat are added at the cooking step, such as Chinese meals, Chinese noodles and soups, foods cooked by using oil and fat as the heating medium, such as Japanese fried foods, fried bean curd, Chinese fried rice, doughnuts and fried dough cakes, oil and fat foods or processed foods to which oil and fat are added at the processing step, such as butter, margarine, mayonnaise, dressings, chocolate, instant noodles, caramels, biscuits and ice creams, and foods onto which oil and fat are sprayed or coated at the processing step, such as sliced and dried rice cakes, hard biscuits and bean-jam buns. Since the extract composed mainly of the compound of the present invention comprises effective ingredients inherently contained in an edible oil and fat or extracts thereof, addition of the extract of the present invention can be easily accomplished and the extract of the present invention can easily added to the above-mentioned foods. Note, the foods are not limited to oil- or and fat-containing foods, and the extract of the present invention can be added to all foods to provide foods having a liver function-improving action, a cholesterol level-reducing action, and a neutral fat level-reducing action.

In the present invention, the amount of the compound of the present invention is not particularly critical, but preferably the amount of the compound of the present invention is 0.001 to 20% by weight, especially 0.01 to 10.0% by weight, based on the food to which the compound of the present invention is added. It the amount of the compound of the present invention is smaller than 0.001% by weight, the effect is low, and if the amount is larger than 20% by weight, the taster and flavor of some foods are adversely affected. Preferably, the content of the compound in the extract is at least 25%. Moreover, the compound of the present invention can be converted to a cyclodextrin inclusion compound and the formed powder can be used.

The significance of the present invention will now be described. Butter is a very popular food prepared from butter fat or cream, a milk solid and a natural colorant, and further, contains sodium chloride. The fat content in butter is usually about 80%. For the preparation of butter, cream obtained by centrifugal separation is subjected to stirring (churning) directly or after lactic acid fermentation, whereby the fat globule membrane is destroyed and fat is fused into particles, and sodium chloride is added to the churned cream and kneading (working) is carried out to obtain a product having a homogeneous texture. The thus-prepared butter is a popular food because of its peculiar and characteristic taste and flavor, but since butter has a very high cholesterol content (the cholesterol level is about 220 mg/100 g), health experts recommend eliminating butter from a food or reducing the content of butter for lowering or controlling the intake of cholesterol. If the compound of the present invention or the extract composed mainly of the compound of the present invention is added to butter, an effect of preventing the increase of the cholesterol level after the intake of butter can be obtained. Moreover, since the product of the present invention is not an imitation food, the inherent taste and flavor of butter can be retained. The compound of the present invention or the extract composed mainly of the compound of the present invention can be added at any step of the butter-preparing process, but the addition at the kneading operation (working) is especially preferable.

The present invention also can be applied to the improvement of a food quality. Mayonnaise is prepared by mixing edible oil with vinegar by using egg yolk lecithin as an emulsifier, and sugar, table salt, mustard and white pepper are used as additives. Mayonnaise and dressings are o/w type emulsions in which the water layer is a main component, and according to JAS standards, mayonnaise is defined as a product having an oil content, which is formed by using an egg as the emulsifier, and dressings are divided into a salad dressing having an oil content of at least 65%, for which an emulsifier other than an egg can be used, and a French dressing formed without using egg. Here, a problem resides in the use of the egg yolk as the emulsifier. It has been experimentally proved that the serum cholesterol level in the human body is increased by the intake of egg yolk. Therefore, the use of a large quantity of egg yolk to increase the quality of mayonnaise is not allowed. Nevertheless, if the compound of the present invention or the extract composed mainly of the compound of the present invention is added to edible oil used for mayonnaise, it becomes possible to prevent an increase of the cholesterol level after the intake of mayonnaise, and it also becomes possible to increase the amount of egg yolk used for mayonnaise, and thus increase the quality of the mayonnaise. Furthermore, the quality of a salad dressing prepared by using egg yolk as the emulsifier can be improved by incorporating the compound or extract of the present invention.

The effect of the compound of the present invention or the extract composed mainly of the compound of the present invention as the functional factor can be increased by a combined use thereof with other substances, and the combined use of a fatty acid having 16 to 20 carbon atoms and 1 to 3 double bonds in the carbon chain, especially $\tau$-linolenic acid (6,9,12-octadecatrienoic acid) or dihomo-$\tau$-linolenic acid (8,11,14-eicosatrienoic acid), is preferred. In this case, the acid can be used directly or in the form a salt of sodium, potassium or ammonium or an ester such as a methyl ester or an ethyl ester. Moreover, oils and fats containing these fatty acids can be used.

The cholesterol level-reducing and neutral fat level-reducing actions of the compound of the present invention, the extract composed mainly of the compound of the present invention, and the food containing the compound or extract have been explained. As described in Japanese Patent Application No. 1-052950, the compound of the present invention or the extract composed mainly of the compound of the present invention can be an inhibitor for specifically inhibiting a $\Delta^5$-desaturase for converting dihomo-$\tau$-linolenic acid to arachidonic acid. It is expected that various pharmacological effects will be obtained by an increase of the eicosanoide of dihomo-$\tau$-linolenic acid brought about by an increase of the content of dihomo-$\tau$-linolenic acid. For example, an antiinflamatory action, an anti-thrombosis action, and a hypotensive action can be expected, and the compound of the present invention and the extract composed mainly of the compound of the present invention can be used as a remedy for related diseases, such as inflammatory diseases, heartvascular and thrombotic diseases, mental diseases, chest and prostate diseases, diabetes, endometritis, malnutrition, menstrual disorders, and malignant tumors. Accordingly, as the function attained by the present invention, there can be mentioned the anti-thrombosis action, the antiinflammatory action, and the hypotensive action. Furthermore, these actions can be significantly enhanced by the effect derived from prostaglandin I by the combined use with $\tau$-linolenic acid and dihomo-$\tau$-linolenic acid.

The compound of the present invention has a very high activity; this is made obvious from the fact that, even if sesamin was continuously administered (oral administration) to 7-weeks-old ICR male mice at a dosage of 2.14 g/day/kg continuously for two weeks, no abnormal symptoms were observed.

The present invention will now be described in detail with reference to the following examples.

EXAMPLE 1

To 16.5 kg of sesame oil was added 94.5 l of hot methanol (60° C.), the mixture was violently stirred to effect extraction, and then allowed to stand at room temperature overnight. The organic solvent was removed from the upper methanol layer by distillation using a rotary evaporator, to obtain 424 g of an extract composed mainly of the compound of the present invention. Then the extract was dissolved in 3.2 l of acetone, the solution was allowed to stand at −80° C. overnight, and the organic solvent was removed by distillation from the filtrate obtained by the filtration to obtain 103 g of an extract composed mainly of the compound of the present invention. When the compound of the present invention was analyzed, it was found that the compound of the present invention comprised 19.6% of sesamin, 30.6% of episesamin and 10.2% of sesaminol and episesaminol based on the extract, and the content of the compound of the present invention in the extract was 60.4%.

Eight-weeks-old male mice (CD-1 mice supplied by Nippon Charles River) were raised for one week with an ordinary feed (CE-2 feed supplied by Nippon Clea). The mice were then divided into 4 groups, each consisting of 10 mice, and the mice of one group were raised with the same ordinary feed, and the mice of the other three groups were raised with a high cholesterol feed having 1% of cholesterol, 0.2% of cholic acid and 5% of olive oil incorporated therein. Of the three groups to which the high-cholesterol feed was given, the two groups were raised with a feed obtained by incorporating 0.4 or 0.6% of the above-mentioned extract composed mainly of the compound of the present invention into the high-cholesterol feed. After two weeks' growth, the mice were fasted for 15 hours and blood was collected. The GOT and GPT activities in the serum were analyzed by an automatic biochemical analysis apparatus (Model 7050 supplied by Hitachi). The results are shown in Table 1, and as seen from these results, increases of GOT and GPT were controlled by using the compound of the present invention.

TABLE 1

| | Ordinary feed | High-cholesterol feed | High-cholesterol feed + 0.4% of sesame oil extract | High-cholesterol feed + 0.6% of sesame oil extract |
|---|---|---|---|---|
| GOT (IU/L) | 72 ± 24.6 | 161 ± 48.8 | 136 ± 53.7 | 104 ± 26.1 |
| GPT (IU/L) | 24 ± 5.5 | 151 ± 66.7 | 68 ± 18.7 | 82 ± 39.1 |

EXAMPLE 2

In the same manner as described in Example 1, mice were raised for one week with the ordinary feed, and the mice were divided into four groups, each consisting of 10 mice. The mice of one group were raised with the same ordinary feed, and the mice of the remaining three groups were raised with a high-cholesterol feed formed by adding 1% of cholesterol, 0.2% of cholic acid and 5% of evening primrose oil to the ordinary feed. A feed formed by adding 0.4 to 0.6% of a purified mixture comprising 61.5% of sesamin and 38.0% of episesamin to the high-cholesterol feed was given to the mice of the two groups among the three groups to which the high-cholesterol feed was given. After two weeks' growth, the mice were fasted for 15 hours and blood was collected. The GOT and GPT activities in the serum were measured, and the results are shown in Table 2. As seen from these results, the increase of GOT by the high-cholesterol feed was controlled by using the mixture of sesamin and episesamin.

TABLE 2

| | Ordinary feed | High-cholesterol feed | High-cholesterol feed + 0.4% of sesamin | High-cholesterol feed + 0.6% of sesamin |
|---|---|---|---|---|
| GOT (IU/L) | 105 ± 31.8 | 141 ± 35.8 | 112 ± 35.6 | 87 ± 13.2 |
| GPT (IU/L) | 29 ± 5.1 | 58 ± 14.2 | 64 ± 23.1 | 45 ± 16.2 |

EXAMPLE 3

Eight-weeks-old male rats of the SD line (supplied by Nippon Clea) were raised for 1 week with an ordinary feed, and the rats were divided into 4 groups, each consisting of 6 rats. The rats of one group were raised with the same ordinary feed, and the rats of the remaining three groups were raised with a high-cholesterol feed comprising 20% of casein, 10% of beef tallow, 59.9% of granulated sugar, 4.0% of a mineral mixture, 0.85% of a vitamin mixture, 4.0% of a filter paper powder, 1.0% of cholesterol and 0.25% of bile acid. A feed formed by adding 1.0 or 2.0% of the mixture of sesamin and episesamin used in Example 2 to the above-mentioned high-cholesterol feed was given to the rats of two groups among the three groups to which the high-cholesterol feed was given. After 1 week's growth, blood was partially collected, and after two weeks' growth, blood was wholly collected. Each blood collection was effected after 17 hours' fasting. The GOT and GPT activities in the serum were measured. The results are shown in Table 3, and from these results, it is seen that the increase of GOT by the high-cholesterol feed was controlled by using the mixture of sesamin and episesamin.

TABLE 3

| | Ordinary feed | High-cholesterol feed | High-cholesterol feed + 1.0% of sesamin | High-cholesterol feed + 2.0% of sesamin |
|---|---|---|---|---|
| After 1 week's raising | | | | |
| GOT (IU/L) | 119 ± 37.8 | 140 ± 48.2 | 76 ± 12.8 | 63 ± 11.5 |
| GPT (IU/L) | 39 ± 9.9 | 23 ± 1.7 | 24 ± 3.4 | 26 ± 1.9 |
| After 2 weeks' raising | | | | |
| GOT (IU/L) | 83 ± 11.5 | 102 ± 37.8 | 81 ± 21.5 | 76 ± 12.1 |
| GPT (IU/L) | 26 ± 4.3 | 21 ± 1.3 | 22 ± 2.3 | 27 ± 6.4 |

EXAMPLE 4

Nine-weeks-old male CDF-1 mice (supplied by Nippon Clea) were raised for 1 week, and the mice were divided into three groups, each consisting of 7 mice. The mice of two groups other than the control group were raised in a chamber filled with air containing 12 ppm of ethanol. After 1 week's growth, the mice were fasted for 16 hours, and blood was collected. The total cholesterol (T-CHO) content, the triglyceride (TG) content, the GOT and GPT activities and the total bilirubin content in the serum were measured, and the results are shown in Table 4.

The increase of the triglyceride content, the total bilirubin content, GOT, and GPT by the administration of the alcohol was significantly reduced. When the general motion of the mice was observed, it was seen that in the ordinary feed-given group, 5 mice of the seven mice were fragged out, but in the sesamin-containing feed-given groups, the motion was not different from the ordinary motion. Thus, a conspicuous difference was found.

TABLE 4

| | Feed intake amount (g/mouse/day) | Sesamin intake amount (mg/mouse/day) | Serum total serum CHOL (mg/dl) | Serum TG (mg/dl) | Serum total BIL (mg/dl) | Serum GOT (IU/L) | Serum GPT (IU/L) |
| --- | --- | --- | --- | --- | --- | --- | --- |
| Ordinary feed | 3.55 | 0 | 91.6 ± 8.8 | 58.6 ± 12.1 | 0.47 ± 0.15 | 149.7 ± 76.3 | 26.1 ± 7.8 |
| Ordinary feed + ethanol | 2.45 | 0 | 100.9 ± 10.2 | 237.3 ± 124.2++ | 1.61 ± 1.32+ | 312.4 ± 203.8+ | 39.6 ± 31.9 |
| Ordinary feed + ethanol + + 1% of sesamin | 2.43 | 24.3 | 89.4 ± 8.5 | 83.0 ± 19.0*+ | 0.41 ± 0.04* | 81.6 ± 15.4**+ | 18.3 ± 1.6* |

Note
CHOL: cholesterol
TG: triglyceride
BIL: bilirubin
to ordinary feed: +P < 0.05 ++P < 0.01
to ordinary feed + ethanol: *P < 0.05 **P < 0.01

EXAMPLE 5

Eight-weeks-old male CDF-1 mice (supplied by Nippon Clea) were raised for 1 week and were divided into three groups, each consisting of 7 mice. To two groups other than the control group, 1 mg/kg of carbon tetrachloride was administered in the abdominal cavity. To one of these two groups, simultaneously, 100 mg/kg of sesamin was forcibly orally administered. Then the mice were fasted for 16 hours and blood was collected. The total cholesterol (T-CHO), the triglyceride (TG) content, GOT, GPT and the total bilirubin content in the serum were measured. The results are shown in Table 5.

TABLE 5

| | Evaluation of Resistance to Acute Loading of Carbon Tetrachloride | | | | | |
| --- | --- | --- | --- | --- | --- | --- |
| | T-CHO (MG/DL) | TG (MG/DL) | GOT (IU/L) | GPT (IU/L) | ALP (IU/L) | T-BIL (MG/DL) |
| Control | 105.00 ± 6.19 | 76.00 ± 8.27 | 122.9 ± 48.6 | 22.1 ± 4.9 | 227.40 ± 18.48 | 0.40 ± 0.13 |
| Carbon tetrachloride | 63.30 ± 6.92 | 48.90 ± 11.6 | 26468.0 ± 2071.6 | 28152.0 ± 1315.4 | 455.90 ± 45.37 | 2.90 ± 0.24 |
| Carbon tetrachloride + sesamin | 84.00 ± 11.99** | 5.70 ± 5.50* | 25274.0 ± 2398.0 | 31750.0 ± 3731.2 | 500.90 ± 36.51 | 1.30 ± 0.42*** |

Note
*p < 0.05 vs. CC14
**p < 0.01 vs. CC14
***p < 0.001 vs. CC14

EXAMPLE 6

Male rats of the Wister line were divided into two groups (control group and sesamin group), each consisting of 6 rats. The rats of the control group were raised for 22 days with a basic feed and the rats of the sesamin group were raised for 22 days with a feed formed by adding 0.5% of sesamin to the basic feed. The rats were fasted overnight, and 1 g/kg of ethanol (20%) was forcibly orally administered. After 1 and 3 hours, blood was collected from the tail vein and the alcohol concentration in blood was measured. After 1 hour from the point of the administration, the ethanol concentration was 0.5 mg/ml in the control group but the ethanol concentration was 0.27 mg/ml in the sesamin group. After 3 hours from the point of the administration, the ethanol concentration was 0.12 mg/ml in the control group but the ethanol concentration was 0.02 mg/ml in the sesamin group. Accordingly, it was confirmed that ethanol disappeared more quickly in the sesamin group than in the control group.

EXAMPLE 7

Examples of the formulation of the compound of the present invention will now be described, though the present invention is not limited by these formulation examples.

FORMULATION 1

With 20.5 g of silicic anhydride was mixed 0.5 g of the compound of the present invention, and 79 g of corn starch was added to the mixture. Then, 100 ml of a 10% solution of hydroxypropyl cellulose in ethanol was added to the mixture, and according to customary procedures, the mixture was kneaded, extruded and dried to obtain a granule.

FORMULATION 2

With 20 g of silicic anhydride was mixed 7 g of the compound of the present invention, and 10 g of microcrystalline cellulose, 3.0 g of magnesium stearate and 60 g of lactose were added to the mixture. The mixture was formed into tablets having a diameter of 7 mm and a weight of 100 mg by using a single-shot tableting machine.

FORMULATION 3

In 200 g of a nonionic surface active agent (TO-10M supplied by Nikko Chemicals) was dissolved 2.5 g of the compound of the present invention under heating at 122° C. Then, 4.8985 g of a sterilized physiological saline solution was added to the solution and the mixture was thoroughly stirred. The liquid was sterilely distributed into vials, and the vials were sealed to obtain injections.

EXAMPLE 8

In 180 ml of salad oil was dissolved 0.9 g of the extract composed mainly of the compound of the present invention, which was obtained in Example 1. Separately, a vessel was charged with one egg yolk, 3 g of table salt, 1 g of mustard, sugar, a spice and a chemical seasoning, and 3 ml of vinegar was added into the vessel and the mixture was strongly stirred by a whip to form a mayonnaise base. Then, 12 ml of vinegar and 180 ml of the salad oil containing the compound of the present invention dissolved therein were added to the mayonnaise base with stirring to obtain a mayonnaise containing the compound of the present invention.

EXAMPLE 9

To 100 g of a butter milk-free butter fat obtained at the stirring operation (churning) in the butter-preparing process, 2 g of the extract composed mainly of the compound of the present invention, which was obtained in Example 1 of the present invention, was added, and the mixture was subjected to the kneading operation (working) to obtain a butter containing the compound of the present invention, which had a homogeneous texture.

EXAMPLE 10

The mayonnaise containing the compound of the present invention, which was obtained in Example 8, and the butter containing the compound of the present invention, which was obtained in Example 9, were compared with the mayonnaise and butter prepared without adding the compound of the present invention, and the differences of the taste and flavor were evaluated by five experts. As a result, it was confirmed that the inherent quality was not influenced by the addition of the compound of the present invention.

EXAMPLE 11

Four-weeks-old male rats of the SD line were raised for 3 weeks with a feed containing 10% of the butter containing the compound of the present invention, which was obtained in Example 9 (compound-added group), or a butter not containing the compound of the present invention (compound-free group). After 3 weeks, the body weight, the liver weight, the plasma cholesterol content, the plasma triglyceride content and the plasma phospholipid content were measured. The results are shown in Table 6.

As apparent from the results shown in Table 6, even if the food containing the compound of the present invention was given, there was no difference of the increase of the body weight or the liver weight during 3 weeks' raising and the growth was not influenced at all. Furthermore, the cholesterol and triglyceride levels in the plasma were reduced by giving the food containing the compound of the present invention.

TABLE 6

| | Compound-added group | Compound-free group |
|---|---|---|
| Initial body weight (g) | 102 ± 3 | 103 ± 3 |
| Final body weight (g) | 272 ± 13 | 275 ± 11 |
| Body weight increase (g) | 170 ± 11 | 172 ± 10 |
| Body weight increased per day (g/day) | 8 ± 0 | 8 ± 0 |
| Total intake (g) | 388 ± 9 | 384 ± 13 |
| Intake per day (g/day) | 18 ± 1 | 18 ± 1 |
| Feed efficiency | 0.43 ± 0.01 | 0.43 ± 0.01 |
| Liver weight (g) | 15.23 ± 0.52 | 14.87 ± 0.67 |
| Plasma cholesterol level (mg/dl) | 76.2 ± 4.3 | 112.7 ± 4.9 |
| Plasma triglyceride level (mg/dl) | 145.7 ± 21.5 | 214.3 ± 11.4 |
| Plasma phospholipid level (mg/dl | 211.4 ± 7.6 | 251.8 ± 17.9 |

EXAMPLE 12

From the extract composed mainly of the compound of the present invention, which was obtained in Example 1, $\Delta^5$-desaturase inhibitors, i.e., sesamin, episesamin, sesaminol and episesaminol, were obtained according to the method described in Japanese Patent Application No. 1-052950. Sesamine-containing mayonnaise and sesamin-containing butter were prepared in the same manner as described in Examples 7 and 8 by using 0.54 g and 1.2 g of sesamin, respectively. Similarly, foods containing the compounds, of the present invention singly or in combination were be obtained. The compound of the present invention was a colorless (white) crystal and had no taste or smell. Accordingly, the compound of the present invention did not have any influence on the inherent quality of the foods.

EXAMPLE 13

To 20 ml of water was added 2 g of $\beta$-cyclodextrin, and 0.2 g of sesamin dissolved in a small amount of acetone was added to the mixture under agitation by a stirrer. The mixture was stirred at room temperature for 4 hours and freeze-dried to obtain 2.2 g of a cyclodextrin inclusion compound containing 10% of sesamin. A sesamin-containing juice was prepared by adding 1 g of the obtained powder to 100 ml of a juice.

EXAMPLE 14

The procedures of Example 13 were repeated by using the compound of the present invention and the extract composed mainly of the compound of the present invention. Juices containing the compound of the present invention and the extract, respectively, were obtained.

EXAMPLE 15

In 82 g of a starting oil and fat material comprising 30% of edible hardened soybean oil, 10% of edible hardened cotton seed oil, 40% of soybean salad oil, 10% of palm oil and 10% of corn oil, 1 g of sesamin was incorporated and dissolved. Then, 15 g of water, 1.2 g of table salt, 0.3 g of monoglyceride, 0.1 g of lecithin, a trace of carotene, 0.00001 g of a flavor and 1.4 g of a milk solid were added to the solution, and the mixture was emulsified, rapidly cooled, and kneaded to obtain a sesamin-containing margarin.

We claim:

1. A method for the prevention or treatment of fatty liver, liver disorders caused by alcohol, treatment of liver disorders caused by chemicals, acceleration of alcohol metabolism, or decrease of serum cholesterol or neutral fat comprising administering to a person in need of such treatment, an effective amount to prevent or treat fatty liver, liver disorders caused by alcohol, to treat liver disorders caused by chemicals, to accelerate alcohol metabolism, or to decrease serum cholesterol or neutral fat of a dioxabicyclo[3.3.0]octane derivative represented by the following general formula (I):

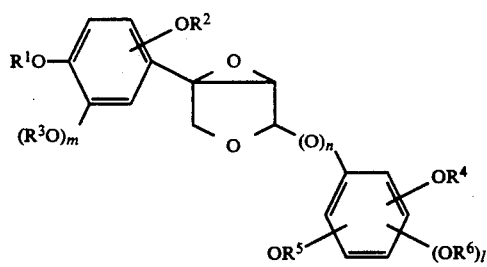

wherein $R^1$, $R^2$, $R^3$, $R^4$, $R^5$ and $R^6$ independently represent a hydrogen atom or an alkyl grouping having 1 to 3 carbon atoms, or $R^1$ and $R^2$ and/or $R^4$ and $R^5$ together form a methylene group or an ethylene group, and n, m and l are 0 or 1.

2. The method as set forth in claim 1, wherein the dioxabicyclo[3.3.0]octane derivative is sesamin, sesaminol, episesamin, episesaminol, sesamolin, 2-(3,4-methylenedioxy-phenyl)-6-(3-methoxy-4-hydroxyphenyl)-3,7-dioxabicyclo [3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

3. The method according to claim 1, wherein a compound of the formula (I) is incorporated into a food or drink.

4. A method for lowering a glutamic-oxaloacetic aminotransferase or glutamic-pyruvic aminotransferase value increased by a high cholesterol diet, comprising administering to a person in need of such treatment, an effective amount to lower a glutamic-oxaloacetic aminotransferase or glutamic-pyruvic aminotransferase value increased by a high cholesterol diet of a dioxabicyclo[3.3.0]octane derivative represented by the following general formula (I):

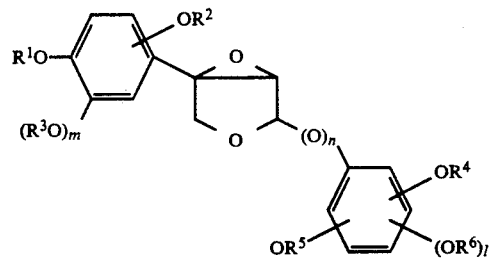

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

5. The method as set forth in claim 4, wherein the dioxabicyclo[3.3.0]octane derivative is sesamin, sesaminol, episesamin, episesaminol, sesamolin, 2-(3,4-methylenedioxy-phenyl)-6-(3-methoxy-4-hydroxyphenyl)-3,7-dioxabicyclo [3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

6. The method according to claim 4, wherein a compound of the formula (I) is incorporated into a food or drink.

7. A method of decreasing glutamic-oxaloacetic aminotransferase, glutamic-pyruvic aminotransferase, serum total cholesterol, serum triglyceride or serum total bilirubin increased by an intake of alcohol, comprising administering to a person in need of such treatment, an effective amount to decrease glutamic-oxaloacetic aminotransferase, glutamic-pyruvic aminotransferase, serum total cholesterol, serum triglyceride or serum total bilirubin to increase by an intake of alcohol of a dioxabicyclo[3.3.0]octane derivative represented by the following general formula (I):

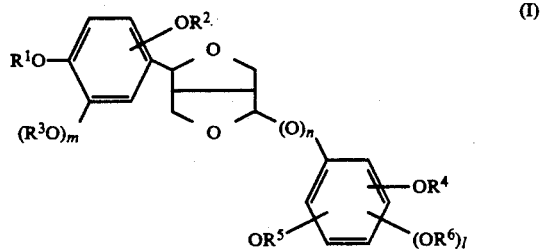

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

8. The method as set forth in claim 7, wherein the dioxabicyclo[3.3.0]octane derivative is sesamin, sesaminol, episesamin, episesaminol, sesamolin, 2-(3,4-methylenedioxy-phenyl)-6-(3-methoxy-4-hydroxyphenyl)-3,7-dioxabicyclo [3.3.0]octane, 2,6-bis-(3-methoxy-4-hydroxyphenyl)-3,7-dioxabicyclo[3.3.0]octane or 2-(3,4-methylenedioxyphenyl)-6-(3-methoxy-4-hydroxyphenoxy)-3,7-dioxabicyclo[3.3.0]octane.

9. The method according to claim 7, wherein a compound of the formula (I) is incorporated into a food or drink.

10. A method of decreasing serum total bilirubin increased by an intake of chemicals, comprising administering to a person in need of such treatment, an effective amount to decrease serum total bilirubin increased by an intake of chemicals of a dioxabicyclo[3.3.0]octane derivative represented by the following general formula (I):

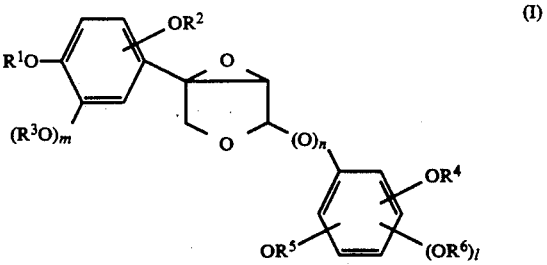

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

11. The method as set forth in claim 10, wherein the dioxabicyclo[3.3.0]octane derivative is sesamin, sesaminol, episesamin, episesaminol, sesamolin, 2-(3,4-methylenedioxy-phenyl)-6-(3-methoxy-4-hydroxyphenyl)-3,7- dioxabicyclo[3.3.0] octane, 2,6-bis-(3-methoxy-4-hydroxyphenyl)-3,7-dioxabicyclo [3.3.0]octane or 2-(3,4-methylene dioxyphenyl)-6-(3-methoxy-4-hydroxyphenoxy)-3,7-dioxabicyclo[3.3.0]octane.

12. The method according to claim 10, wherein a compound of the formula (I) is incorporated into a food or drink.

13. A method of accelerating the lowering of a serum alcohol level increased by an intake of alcohol, comprising administering to a person in need of such treatment, an effective amount to accelerate the lowering of a serum alcohol level increased by an intake of alcohol of a dioxabicyclo[3.3.0]octane derivative represented by the following general formula (I):

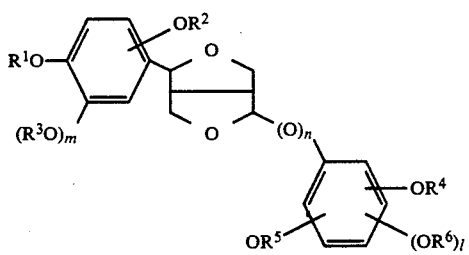

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

14. The method as set forth in claim 13, wherein the dioxabicyclo[3.3.0]octane derivative is sesamin, sesaminol, episesamin, episesaminol, sesamolin, 2-(3,4-methylenedioxy-phenyl)-6-(3-methoxy-4-hydroxyphenyl)-3,7-dioxabicyclo [3.3.0]octane, 2,6-bis-(3-methoxy-4-hydroxyphenyl)-3,7-dioxabicyclo[3.3.0]octane or 2-(3,4-methylene dioxyphenyl)-6-(3-methoxy-4-hydroxyphenoxy)-3,7-dioxabicyclo[3.3.0]octane.

15. The method according to claim 13, wherein a compound of the formula (I) is incorporated into a food or drink.

16. A method of lowering a cholesterol or triglyceride level in the plasma, comprising administering to a person in need of such treatment an effective amount to lower a cholesterol or triglyceride level in the plasma of dioxabicyclo[3.3.0]octane derivative represented by the following general formula (I):

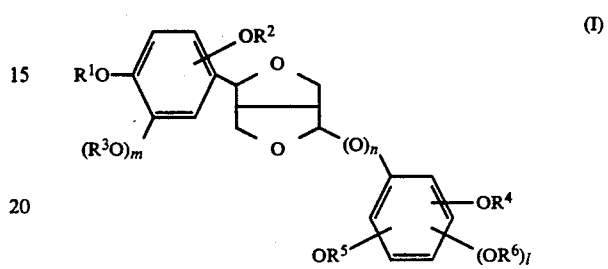

wherein $R^1$, $R^2$, $R^3$, $R^4$, $R^5$ and $R^6$ independently represent a hydrogen atom or an alkyl group having 1 to 3 carbon atoms, or $R^1$ and $R^2$ and/or $R^4$ and $R^5$ together form a methylene group or an ethylene group, and n, m and l are 0 or 1.

17. The method as set forth in claim 16, wherein the dioxabicyclo[3.3.0]octane derivative is sesamin, sesaminol, episesamin, episesaminol, sesamolin, 2-(3,4-methylenedioxy-phenyl)-6-(3-methoxy-4-hydroxyphenyl)-3,7-dioxabicyclo[3.3.0] octane, 2,6-bis-(3-methoxy-4-hydroxyphenyl)-3,7-dioxabicyclo [3.3.0]octane or 2-(3,4-methylene dioxyphenyl)-6-(3-methoxy-4-hydroxyphenoxy)-3,7-dioxabicyclo[3.3.0]octane.

18. The method according to claim 16, wherein a compound of the formula (I) is incorporated into a food or drink.

* * * * *

UNITED STATES PATENT AND TRADEMARK OFFICE
CERTIFICATE OF CORRECTION

PATENT NO. : 5,211,953
DATED : May 18, 1993
INVENTOR(S) : Yoshifumi SHINMEN et al It is certified that error appears in the above-indentified patent and that said Letters Patent is hereby corrected as shown below:

In claim 1, at column 13, lines 3-14; claim 4, at colunm 13, lines 41-52; claim 7 at column 14, lines 12-23; claim 10, at colunm 14, lines 47-59; claim 13, at column 15, lines 16-28; and claim 16 at colunm 16, lines 12-23, delete Formula (I) as it appears and insert therefor

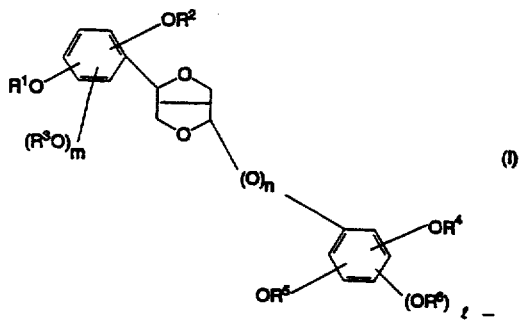

Signed and Sealed this

Sixth Day of December, 1994

Attest:

BRUCE LEHMAN

Attesting Officer    Commissioner of Patents and Trademarks